United States Patent [19]

Grochal et al.

[11] Patent Number: 4,696,337
[45] Date of Patent: Sep. 29, 1987

[54] APPARATUS FOR ANTICIPATION OF STRUCTURE OF CASTING ALLOYS AND PARTICULARLY THE DEGREE OF SPHEROIDIZATION OF CAST IRON

[75] Inventors: Tadeusz Grochal, Wieliczka; Roman Ryglicki; Wojciech Wierzchowski, both of Cracow, all of Poland

[73] Assignee: Instytut Odlewnictwa, Cracow, Poland

[21] Appl. No.: 920,561

[22] Filed: Oct. 17, 1986

[30] Foreign Application Priority Data

Oct. 31, 1985 [PL] Poland .................................. 256069

[51] Int. Cl.4 ..................... B22D 2/00; B22D 27/02; B22D 46/00
[52] U.S. Cl. ..................................... 164/150; 164/154; 324/65 P
[58] Field of Search ................ 164/150, 154, 4.1, 457; 324/65 P, 65 R

[56] References Cited

U.S. PATENT DOCUMENTS 4,173,299 11/1979 Kollberg ........................ 164/4.1 X
4,333,512 6/1982 Sugiura .......................... 164/150 X

FOREIGN PATENT DOCUMENTS 2933163 2/1980 Fed. Rep. of Germany ...... 164/150
44-4399 2/1969 Japan .................................. 164/4.1

Primary Examiner—J. Reed Batten, Jr.
Attorney, Agent, or Firm—Ladas & Parry

[57] ABSTRACT

The apparatus has a supply system 1 and measuring system 2, connected via suitable electrodes to the mould 3. This mould 3 has a cylindrical shape and a cylindrical pouring cup. The cavity of the mould 3 has been divided by vertical walls 4 and 5 into three parts in such a way that the wall 4 divides the mould 3 into two halves and the wall 5, in turn, divides one of the halves also into two equal parts. The electrodes of the supply system 1 and measuring system 2 have been mounted in the bottom of the mould 3 in the portions delimited by the wall 5. The shape of the mould ensures a directional solidification of the specimens contained therein. Owing to this a compact specimen is obtained without shrinkage porosities and contraction cavities over the measuring length. The structure of the alloy is anticipated from the curve of variations of voltage signal during the period from the moment of pouring of liquid metal into the mould 3 to the moment of solidification of the specimen.

2 Claims, 3 Drawing Figures

U.S. Patent Sep. 29, 1987 4,696,337
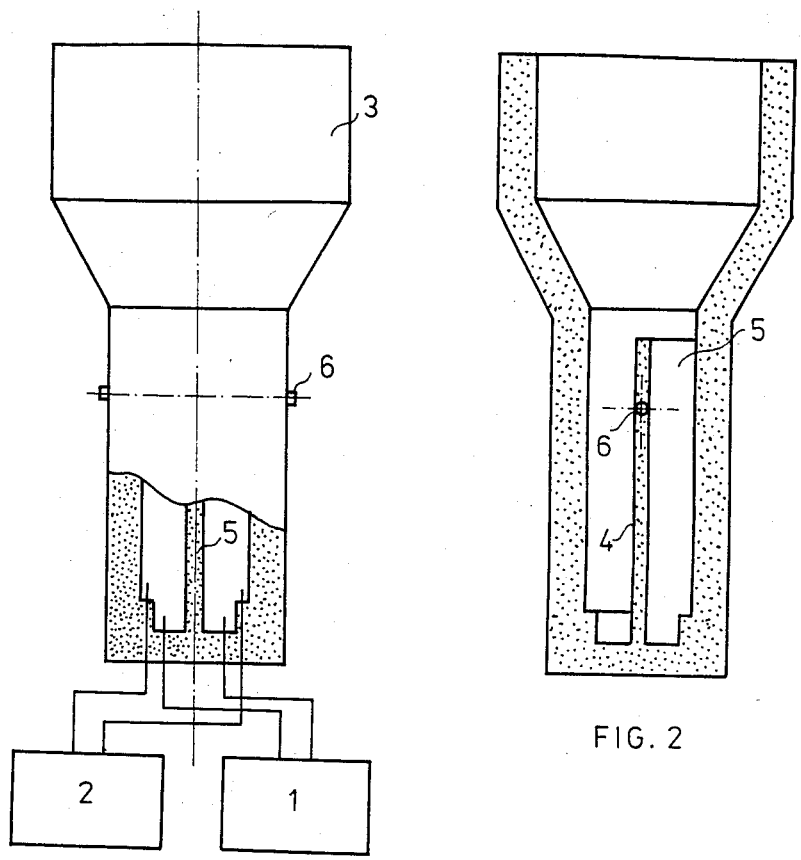
FIG. 1
FIG. 2
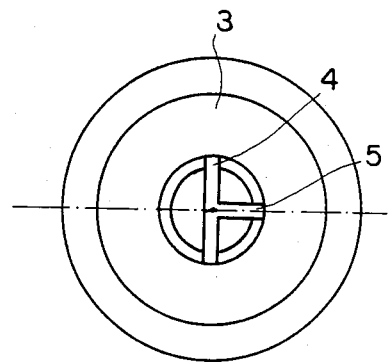
FIG. 3

APPARATUS FOR ANTICIPATION OF STRUCTURE OF CASTING ALLOYS AND PARTICULARLY THE DEGREE OF SPHEROIDIZATION OF CAST IRON

This invention relates to an apparatus making possible anticipation of the structure of casting alloys before pouring liquid alloy to the mould.

The invention is applicable in iron and steel industry and metal-forming industry.

For the time being, in order to determine effectiveness of metallurgical processes one should investigate the structure of a sample in solid state using chemical analyses methods and microscopic observation. Also known are methods of microscopic observation of metallographic specimens produced in a rapid way by means of special equipment, as well as methods of determination of structure consisting in measurement of specific resistance of an alloy in solid state. The methods so far known are not objective and, what is more, they don't make possible an improvement of the structure of an alloy prior to pouring it into the mould, if necessary.

No apparatuses making possible anticipation of the structure of metal alloy have been so far known. This invention is aimed at making possible an estimate of the future structure of metal alloy, and especially the degree of spheroidization of cast iron, when this alloy is in liquid state. Information on the future structure of the alloy would make possible, if required, an intervention by a production engineer before the liquid metal is poured into the mould. This aim has been achieved due to apparatus according to this invention. In this apparatus use has been made of the known phenomenon of voltage drop of electric current flowing through a resistance. In the apparatus according to the invention this resistance is made of a specimen of liquid metal. The value of resistance of the specimen varies depending upon the structure and temperature.

The nature of the solution consists in that both the supply and measuring systems are connected to a casting mould having a special shape. This mould has a cylindrical shape and a cylindrical pouring cup. The cross section area of this pouring cup is considerably greater than that of the cylindrical cavity in the mould. The mould cavity is divided by vertical walls into three parts. One wall divides the mould cavity into two halves, while the second one divides, in turn the second half of it into two equal parts. The height of the partition wall dividing the mould is smaller than the height of the cylindrical mould cavity. Electrodes of the supply and measuring systems are built into the mould bottom in the portions delimited by the smaller wall. This shape of mould ensures a directional solidification of the specimens contained in it. Owing to this the specimens obtained have no shrinkage porosity and contraction cavities over the measuring length. The measuring length consists of both smaller specimens, that is it is equal to the double distance of electrodes of measuring system from the bottom lug edge. The greater specimen is necessary for ensuring directional solidification of both smaller specimens. The cross section area of the pouring cup is so great as compared with the cross section area of the specimens that the value of its resistance is negligible and does not distort the results of the measurements.

The shape of the specimen and solidification conditions leads to a similar solidification of the specimen as in industrial conditions and, in consequence, the results of investigations may be referred directly to the alloys produced in industrial conditions. In order to increase accuracy of measurements one may record simultaneously the thermal solidification curve. The apparatus can be supplied either with direct current, or with alternating current.

The apparatus according to the invention shown on an example of embodiment has been presented on the accompanying drawing, wherein FIG. 1 presents the lay-out of the apparatus, FIG. 2 visualizes the vertical section of the mould, and FIG. 3 presents the top view of the mould.

The apparatus according to the invention consists of a supply system 1, measuring system 2 and mould 3. The mould 3 has a cylindrical shape and is terminated at the top with a cylindrical pouring cup with cross section area exceeding considerably the cross section area of the cavity of the mould 3. The cylindrical cavity of mould 3 has been divided by vertical walls 4 and 5. The wall 4 divides the cavity of the mould 3 into two halves, and the wall 5, in turn divides one of these cavity halves also into two equal parts. The height of the walls 4 and 5 is smaller than that of the cylindrical cavity of the mould 3.

In the presented example of embodiment in the wall 4 in its mid-height there is mounted a thermocouple 6 connected to a recorder. The supply system 1 and the measuring system 2 are connected to the mould 3 via suitable electrodes which are mounted in the bottom of the mould 3 in the portions delimited by the wall 5. Operation of the apparatus according to the invention is as follows:

The supply system 1 is to be switched on. Liquid metal alloy is to be poured into the mould 3 which closes electric circuit and, in consequence, switches on the measuring system 2.

Supply system 1 supplies the apparatus with electric current with a constant intensity, irrespective of the changes taking place in the specimen of metal alloy. Measuring system 2 measures and records variations of voltage signal over the resistance being the specimen investigated and simultaneously thermocouple 6 measures temperature variations. After solidification of the alloy in the mould 3 the supply system 1 is switched off.

Analysis of the obtained curves of voltage signal and temperature variations enables the structure of the alloy to be determined. Determination of the structure is based on the variations of voltage signal from the moment of pouring of liquid metal to the mould to solidification of specimen. In order to increase accuracy of measurement temperature variations are simultaneously recorded.

Analysing both curves one can quickly and univocally determine changes occurring in the alloy during its solidification and thus foresee the structure of the alloy. This makes possible to obtain an alloy having the required structure and thus diminish the number of rejects and misfit casts, which is of major economic importance.

We claim:

1. Apparatus for anticipation of the structure of casting alloys and, particularly, the degree of spheroidization of cast iron, the apparatus comprising a cylindrical casting mould having a mould cavity and provided with a cylindrical pouring cup having a cross sectional area greater than that of the mould cavity; a first vertical wall which divides the mould cavity into two equal halves; a second vertical wall which divides one of the two equal halves into two equal parts, the first and second vertical walls having a height less than the height of the mould cavity; electrodes built in the bottom of the mould and projecting into each of the two equal parts delimited by the second vertical wall; a supply system connected to suitable electrodes; and a measuring system connected to suitable electrodes.

2. The apparatus as set forth in claim 1, further comprising a thermocouple mounted in the first vertical wall.

* * * * *